(12) United States Patent
Khaled

(10) Patent No.: US 7,335,384 B2
(45) Date of Patent: Feb. 26, 2008

(54) NUTRIENT COMPOSITIONS FOR THE TREATMENT AND PREVENTION OF INFLAMMATION AND DISORDERS ASSOCIATED THEREWITH

(75) Inventor: F. Mahnaz Khaled, Indian Springs, AL (US)

(73) Assignee: 4K Nutripharma International, Indian Springs, AL (US)

( * ) Notice: Subject to any disclaimer, the term of this patent is extended or adjusted under 35 U.S.C. 154(b) by 137 days.

(21) Appl. No.: 11/378,718

(22) Filed: Mar. 17, 2006

(65) Prior Publication Data
US 2007/0218042 A1    Sep. 20, 2007

(51) Int. Cl.
A61K 31/525    (2006.01)
A61K 31/4415   (2006.01)
A61K 31/714    (2006.01)
A61K 31/737    (2006.01)
A61K 31/095    (2006.01)
A61K 31/10     (2006.01)
A61K 31/191    (2006.01)
A61K 31/194    (2006.01)
A61K 31/197    (2006.01)
A61K 31/28     (2006.01)
A61P 19/02     (2006.01)
A61P 25/06     (2006.01)

(52) U.S. Cl. ............... 424/681; 424/639; 424/641; 424/643; 424/682; 424/692; 424/697; 424/702; 424/94.1; 514/44; 514/46; 514/52; 514/54; 514/55; 514/62; 514/249; 514/251; 514/276; 514/345; 514/355; 514/387; 514/440; 514/458; 514/474; 514/492; 514/494; 514/554; 514/556; 514/562; 514/563; 514/574; 514/689; 514/706; 514/711; 514/725; 514/763; 514/825; 514/904

(58) Field of Classification Search .......... 424/681, 424/682; 514/825, 904
See application file for complete search history.

(56) References Cited

U.S. PATENT DOCUMENTS

| | | | |
|---|---|---|---|
| 6,068,999 A | 5/2000 | Hendrix | |
| 6,159,505 A | 12/2000 | Piper | |
| 6,465,517 B1 | 10/2002 | Van Der Zee | |
| 6,500,450 B1 | 12/2002 | Hendrix | |
| 6,506,413 B1* | 1/2003 | Ramaekers | 424/535 |
| 6,660,308 B1* | 12/2003 | Martin et al. | 424/728 |
| 6,974,841 B1* | 12/2005 | Rapisarda | 514/783 |
| 2003/0114416 A1 | 6/2003 | Pulaski | |
| 2003/0114418 A1 | 6/2003 | Pulaski | |
| 2004/0048870 A1 | 3/2004 | Amir | |
| 2004/0180106 A1 | 9/2004 | Theoharides | |
| 2005/0186269 A1 | 8/2005 | Udell | |

OTHER PUBLICATIONS

J. Neurol Sci. 1995; 134:9.
Goadsby et al. NEJM 2002; 346:260.
Eur. J. Pharmacol 2001; 421:157.
Med Hypoth 2000; 55:195.

* cited by examiner

Primary Examiner—John Pak
(74) Attorney, Agent, or Firm—Bradley, Arant, Rose & White, LLP

(57) ABSTRACT

The present disclosure describes a novel composition for the treatment and/or prevention of neurogenic inflammation. Such composition is also useful in the treatment and/or prevention of disease states and conditions associated with neurogenic inflammation. Such disease states and conditions include, but are not limited to, migraine headache, arthritis and fibromyalgia. The composition comprises nutrient compounds in a novel combination and formulation to treat and/or prevent neurogenic inflammation and disease states and conditions associated therewith. By reducing neurogenic inflammation, the compositions of the present disclosure reduce the symptoms associated with neurogenic inflammation, such as pain and systemic inflammation in general.

14 Claims, 1 Drawing Sheet

NUTRIENT COMPOSITIONS FOR THE TREATMENT AND PREVENTION OF INFLAMMATION AND DISORDERS ASSOCIATED THEREWITH

FIELD OF THE DISCLOSURE

The present disclosure relates to nutritional supplements. Specifically, the present disclosure relates to nutritional supplements used to treat and/or prevent inflammation and disease states and conditions resulting from inflammation.

BACKGROUND

The human diet has been known for centuries to impact health. For example, gout was determined to be caused by a deficiency in vitamin C which was curable when the diet was modified or supplemented to ensure adequate intake of vitamin C. The use of dietary supplements in the general population is quite common and use of dietary supplements can aid the body in combating diseases while increasing the quality of life of the person taking such supplements.

Inflammation has been associated with a number of disease states and conditions in humans and animals. Two type of inflammation have been recognized in the art-immunogenic inflammation and neurogenic inflammation (also referred to as sterile inflammation since the presence of an infections agent is not required). Immunogenic inflammation arises when an antigen binds to an antibody or leukocyte receptor to trigger an inflammatory cascade. Prior sensitization is required, and the inflammatory response can take several forms including immediate and cell-mediated hypersensitivity. Neurogenic inflammation occurs when an agent triggers the release of inflammatory neuropeptides, such as but not limited to substance P. Neurogenic inflammation can also arise when a nerve impulse travels down an axon to release neurogenic peptides at the terminus. There is an interplay between immunogenic and neurogenic inflammation, in that certain neurogenic peptides can degranulate mast cells, thereby releasing cellular mediators which can activate sensory nerves.

Neurogenic inflammation has been postulated to be involved in a variety of human disease states and conditions, including but not limited to, migraine headache, arthritis, and fibromyalgia. The basis of these conditions may be an acquired neuronal pathway that shunts neurogenic inflammatory stimuli to the cerebral vasculature, joints or muscles, respectively. Migraine headache is a well studied disease in which neurogenic inflammation has been implicated.

According to the National Headache Foundation, one in four households in the United States, or 28 million people, is affected by migraine headaches. Of that total, 11 million people have chronic migraine headaches. Migraine headaches most commonly strike young adult women. The common characteristics are recurrent attacks of headache, with pain occurring most often on one side of the head, accompanied by various combinations of symptoms, such as nausea, vomiting, and sensitivity to light and sound. Migraine headaches can occur at any time of day or night, but occur most frequently occur in the morning. A migraine episode can last from several hours to several days.

Migraine headaches are generally of two types: classic and common. A classic migraine headache is characterized by an "aura" (light spots) or other sensations that are known by the migraineur to occur just prior to the migraine headache itself. A common migraine headache is considered any migraine headache not preceded by an aura or other symptomatic warning to the patient. Migraine headaches are considered a hereditary disease. If both parents have migraine headaches, there is a 75% chance that the offspring will be a "migraineur"; if only one parent has migraine, the chance is as high as 50% that the offspring will be affected.

During a migraine headache, blood vessels in the head go through a cycle of extreme constriction followed by rapid dilation. Nerve pathway changes and imbalances in brain chemistry may cause blood vessels to become inflamed. The interaction between the brain chemistry and blood vessel constriction/dilation is currently debated, but recent research indicates that migraine headaches are caused by alterations in the nerve pathways of the brain, specifically the trigeminal nerve system. When a migraine headache is triggered, the trigeminal nerve releases neuropeptides, such as, but not limited to, substance P and neurotransmitters such as but not limited to serotonin, bradykinin and histamine. These neuropeptides and/or neurotransmitters cause neurogenic inflammation of the brain vasculature and constriction/dilation of the blood vessels which results in migraine pain. Subsequently, trigeminal nerve endings stimulate the release of more neuropeptides and/or neurotransmitters, and a vicious cycle begins. Additionally, altered blood flow affects projections to the visual cortex and visual processing centers that may be associated with the development of aura in many migraine patients.

A variety of causal factors for migraine have been suggested that include, but are not limited to, a deficiency of cerebral magnesium, increased nitric oxide (NO) production and mitochondrial dysfunctions (J Neurol Sci 1995; 134:9). Low cerebral magnesium and/or higher NO production cause platelet aggregation with the subsequent release of serotonin and other neurotransmitters leading to cerebral constriction which may contribute to a migraine attack. Serotonin and other neurotransmitters can also stimulate the release of other pro-inflammatory agents. Furthermore, evidence indicates that impaired mitochondrial energy metabolism in the brain may play a role in the pathology of migraine headaches. Studies indicated that migraine suffers exhibited decreased mitochondrial phosphorylation between migraine attacks, indicating that the mitochondrial energy production was impaired. Specifically, a deficiency in the flavin coenzymes FAD and FMN, which are required by the flavoproteins for efficient mitochondrial electron transport chain, may be implicated in such impaired energy metabolism.

In the past, treatment of migraine has involved non-pharmacologic behavioral modification and physical measures, and pharmacotherapeutic measures. Acute pharmacological drug treatment of migraine may be either to blunt the headache or to reduce the intensity of the attack. Triptans act on serotonin receptors and are currently considered the most important drugs for the acute treatment of migraine. However, when a chronic condition exists characterized by frequent attacks of debilitating pain, a preventive treatment would be desirable. Also, a significant number of patients will benefit from a combined acute and preventative treatment approach.

Preventive medications are usually taken every day in order to reduce the frequency, severity and/or duration of migraine attacks. Patients may prefer such treatments since the frequently recurring migraine significantly interferes with the patients' daily routine. Currently used preventive medications include beta-adrenergic blockers, antidepressants, calcium channel antagonists, serotonin antagonists and anticonvulsants. The doses of the currently used preventative medications required to reduce the frequency of migraine may produce marked and/or intolerable side effects (Goadsby et al. NEJM 2002; 346:260). Therefore, there is a significant need for acute and preventive treatments for migraine suffers and other disease states and conditions associated with neurogenic inflammation that are devoid of said side effects.

The present disclosure provides a composition useful in the treatment and/or prevention of disease states and conditions related to neurogenic inflammation. Furthermore, the present disclosure provides methods of treatment using such compositions. The compositions described are nutritional supplements which are generally recognized as safe for human consumption. Such compositions and methods have heretofore been lacking in the art.

DETAILED DESCRIPTION

Figure 1:
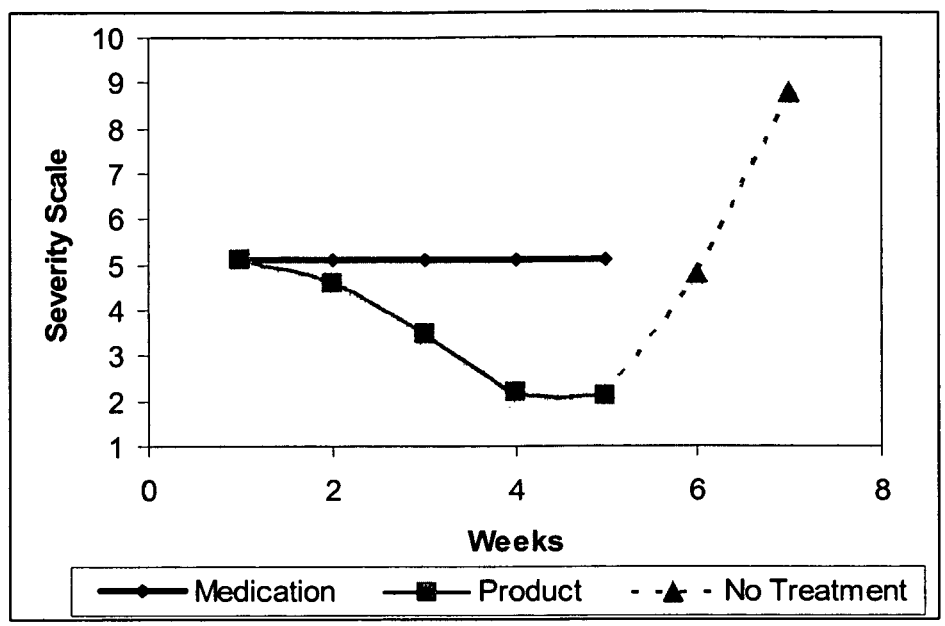
FIG. 1 illustrates the effect of one embodiment of a composition of the present disclosure on the severity of migraine headaches in human subjects during and after treatment. Time is in weeks (x-axis) and severity scale is 1-10 (y-axis), where 1=minor headache and 10=debilitating head ache.

The terms "prevention", "prevent", "preventing", "prevented", "suppression", "suppress", "suppressing" and "suppressed" as used herein refer to a course of action (such as administering a compound or composition) initiated prior to the onset of a symptom, aspect, or characteristics of a disease state or condition so as to prevent or reduce said symptom, aspect, or characteristics. Such preventing and suppressing need not be absolute to be useful.

The terms "treatment", "treat" and "treating" as used herein refer to a course of action (such as administering a compound or composition) initiated after the onset of a symptom, aspect, or characteristics of a disease state or condition so as to eliminate or reduce said symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill as the result of a disease state or condition that is treatable by a method or compound or composition of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill as the result of a disease state or condition that is preventable by a method or compound or composition of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound or composition that is capable of having any detectable effect on any symptom, aspect, or characteristics of a disease state or condition. Such effect need not be absolute to be beneficial.

The term "disease state" as used herein refers to any pathological condition of a cell, a body part, an organ, a tissue or a system resulting from a cause.

The term "condition" as used herein refers to any manifestation, symptom, disorder or state associated with a disease state.

The applicant has discovered a novel composition for the treatment and/or prevention of neurogenic inflammation. Such composition is also useful in the treatment and/or prevention of disease states and conditions associated with neurogenic inflammation. Such disease states and conditions include, but are not limited to, migraine headache, arthritis and fibromyalgia.

The composition comprises nutrient compounds in a novel combination and formulation to treat and/or prevent neurogenic inflammation and disease states and conditions associated therewith. By reducing neurogenic inflammation, the compositions of the present disclosure reduce the symptoms associated with neurogenic inflammation, such as pain and inflammation. In addition the composition of the present disclosure enhances the subject's feelings of wellness and energy.

The composition of the present disclosure comprises an integrated anti-oxidant system. Neurogenic inflammation involving mitochondrial dysfunctions has been postulated as a basis of migraine headache and other disease states and conditions associated with neurogenic inflammation (Ann Neurol 1984; 16:157). In migraine headaches, the roles of low cerebral magnesium (Mg) and nitric oxide (NO) production, including calcium channelopathy, have been implicated to mitochondrial dysfunctions leading to neurogenic inflammation. Serotonin receptors play a major role in nociception (painful episodes) and deficiency of hydroxy-tryptamine, a precursor of serotonin, is associated with migraine and neurogenic inflammation (Neurol 2005; 64:S9). Several B vitamins have been found to act as antinociceptive agents and Vitamin $B_6$ has been shown to increase hydroxy-tryptamine levels. The B vitamins, riboflavin ($B_2$) and cobalamin ($B_{12}$) along with proteoglycans, like glucosamine sulfate, are known to ameliorate the neurogenic inflammation (Eur. J. Pharmacol 2001; 421:157 and Med Hypoth 2000; 55:195). An increase in serum sulfate by ingesting methylsulphonylmethane (MSM) together with glucosamine sulfate has been found to be effective in the treatment of pain syndromes (Altern Med Rev 2002; 7:22). An integrated antioxidative nutrient system is essential in combating systemic inflammatory episodes and CoQ10 is a component in this system.

The composition of the present disclosure comprises, consists of or consists essentially of, riboflavin (vitamin $B_2$), pyridoxine (vitamin $B_6$), cobalamin (vitamin $B_{12}$), Mg, glucosamine sulfate, methylsulfonylmethane and coenzyme Q-10 in the ranges indicated in Table 1.

The forms of the compounds listed above may be varied as known to one of ordinary skill in the art and as set forth herein. In one embodiment, the pyridoxine may be present, at least partially, as pyridoxine HCL or its coenzyme form pyridoxal 5-phosphate; likewise cobalamin may be present, at least partially, as methyl cobalamin or hydroxycobalamin; Mg may be present, at least partially, as its citrate salt. Furthermore, one or more of the components may also be present in a chelated form. In one embodiment, amino acid chelates are used. The chelated forms facilitate a more effective absorption and increased biological activities as well as increased shelf life.

Furthermore, the present disclosure is meant to include as substitutes for the above mentioned compounds, those compounds that are converted into any of the forgoing through the body's physiological processes.

The described composition may also comprise, consist of or consist essentially of at least one of the following: beta carotene, thiamine HCl, ascorbic acid, folate, biotin, vitamin E, zinc (Zn), selenium (Se), manganese, glutathione, niacinamide, N-acetyl-tyrosine, α-lipoic acid, hydroxycitric acid, S-adenosylmethionine, pantothenic acid, and chondroitin sulfate in the ranges indicated in Table 1.

The forms used of the compounds listed above may be varied as known to one of ordinary skill in the art. In one embodiment, vitamin E may be present, at least partially, as it succinate ester; likewise citric acid may be present, at least partially, as the hydroxylated derivative; and glutathione may be present, at least partially, in a reduced form. Furthermore, one or more of the components may also be present in a chelated form. For example, zinc, manganese and/or selenium may be present as an amino acid chelate. The chelated forms facilitate a more effective absorption and increased biological activities as well as increased shelf life.

Furthermore, the present disclosure is meant to include as substitutes for the above mentioned compounds, those compounds that are converted into any of the forgoing through the body's physiological processes.

In one embodiment, the composition comprises riboflavin (vitamin $B_2$) pyridoxine (vitamin $B_6$), cobalamin (vitamin $B_{12}$), Mg, glucosamine sulfate, methylsulfonylmethane, coenzyme Q-10, beta carotene, thiamine, ascorbic acid, folate, biotin, vitamin E, zinc (Zn), selenium (Se), glutathione, niacinamide, N-acetyl tyrosine, α-lipoic acid, hydrocitric acid, S-adenosylmethionine, pantothenic acid, and chondroitin sulfate in the amounts indicated in Table 2.

As discussed above, the forms used of the compounds listed above may be varied as known to one of ordinary skill in the art. In one embodiment, the pyridoxine may be present, at least partially, as pyridoxine HCl or its coenzyme form pyridoxal 5-phosphate, cobalamin may be present, at least partially, as methyl cobalamin or hydroxycobalamin, Mg may be present, at least partially, as its citrate salt, thiamine may be present as the HCl salt, vitamin E may be present, at least partially, as it succinate ester, citric acid may be present, at least partially, as the hydroxylated derivative and glutathione may be present, at least partially, in a reduced form. Furthermore, one or more of the components may also be present in a chelated form. At least one of zinc, manganese and/or selenium may be present as an amino acid chelate. The chelated forms facilitate a more effective absorption and increased biological activities as well as increased shelf life.

Furthermore, the present disclosure is meant to include as substitutes for the above mentioned compounds, those compounds that are converted into any of the forgoing through the body's physiological processes.

The described composition provides a unique formulation of compounds chosen to treat and/or prevent neurogenic inflammation. The unique selection of components has not been heretofore appreciated in the art.

The compounds of the present disclosure may be used to treat neurogenic inflammation, or disease states or conditions associated with neurogenic inflammation. Such disease states and conditions include, but are not limited to, headaches, including but not limited to migraine headaches, arthritis and fibromyalgia.

In one embodiment, the present disclosure describes a method for treating neurogenic inflammation in a subject in need of such treatment, said method comprising administering to said subject a therapeutically effective amount of a composition of the present disclosure.

In an alternate embodiment, the present disclosure describes a method for treating headaches in a subject in need of such treatment, said method comprising administering to said subject a therapeutically effective amount of a composition of the present disclosure. In a specific embodiment, the headaches may be migraine headaches.

In yet another alternate embodiment, the present disclosure describes a method for treating arthritis in a subject in need of such treatment, said method comprising administering to said subject a therapeutically effective amount of a composition of the present disclosure.

In still another embodiment, the present disclosure describes a method for treating fibromyalgia in a subject in need of such treatment, said method comprising administering to said subject a therapeutically effective amount of a composition of the present disclosure.

In a further embodiment, the present disclosure describes a method for reducing inflammatory mediators in a subject in need of such reduction, said method comprising administering to said subject a therapeutically effective amount of a composition of the present disclosure. In one embodiment, the inflammatory mediator is a thromboxane, such as thromboxane $B_2$.

The compounds of the present disclosure may also be used to prevent neurogenic inflammation, or disease states or conditions associated with neurogenic inflammation. Such disease states and conditions include, but are not limited to, headaches, including but not limited to migraine headaches, arthritis and fibromyalgia.

In one embodiment, the present disclosure describes a method for preventing neurogenic inflammation in a subject in need of such prevention, said method comprising administering to said subject a therapeutically effective amount of a composition of the present disclosure.

In an alternate embodiment, the present disclosure describes a method for preventing headaches in a subject in need of such prevention, said method comprising administering to said subject a therapeutically effective amount of a composition of the present disclosure. In a specific embodiment, the headaches may be migraine headaches.

In yet another alternate embodiment, the present disclosure describes a method for preventing arthritis in a subject in need of such prevention, said method comprising administering to said subject a therapeutically effective amount of a composition of the present disclosure.

In still another embodiment, the present disclosure describes a method for preventing fibromyalgia in a subject in need of such prevention, said method comprising administering to said subject a therapeutically effective amount of a composition of the present disclosure.

In a further embodiment, the present disclosure describes a method for preventing the formation inflammatory mediators in a subject in need of such prevention, said method comprising administering to said subject a therapeutically effective amount of a composition of the present disclosure. In one embodiment, the inflammatory mediator is a thromboxane, such as thromboxane $B_2$.

In each of the methods of treatment and prevention described above, any composition of the present disclosure may be used. In one embodiment, such composition comprises, consists of or consists essentially of riboflavin (vitamin $B_2$), pyridoxine (vitamin $B_6$), cobalamin (vitamin $B_{12}$), Mg, glucosamine sulfate, methylsulfonylmethane and coenzyme Q-10 in the ranges indicated in Table 1. In an alternate embodiment, the composition comprises, consists of or consists essentially of riboflavin (vitamin $B_2$) pyridoxine (vitamin $B_6$), cobalamin (vitamin $B_{12}$), Mg, glucosamine sulfate, methylsulfonylmethane and coenzyme Q-10 plus at least one of the following: beta carotene, thiamine HCl, ascorbic acid, folate, biotin, vitamin E, zinc (Zn), manganese (Mn) selenium (Se), glutathione, niacinamide, N-acetyl-tyrosine, α-lipoic acid, hydroxycitric acid, S-adenosylmethionine, pantothenic acid, and chondroitin sulfate in the ranges indicated in Table 1. In yet another alternate embodiment, the composition comprises, consists of or consists essentially of riboflavin (vitamin $B_2$) pyridoxine (vitamin $B_6$), cobalamin (vitamin $B_{12}$), Mg, glucosamine sulfate, methylsulfonylmethane and coenzyme Q-10 plus at least one of beta carotene, thiamine HCl, ascorbic acid, folate, biotin, vitamin E, zinc (Zn), manganese (Mn) selenium (Se), glutathione, niacinamide, N-acetyl-tyrosine, α-lipoic acid, hydrocitric acid, S-adenosylmethionine, pantothenic acid, and chondroitin sulfate in the amounts listed in Table 2.

The present disclosure describes the application of the composition and methods to the treatment and/or prevention of migraine headaches, arthritis and fibromyalgia and symptoms associated with the foregoing. As discussed above, migraine headaches, arthritis and fibromyalgia have been associated with the pathogenesis of neurogenic inflammation.

Methods of Administration

The compositions of the present disclosure can be administered by any conventional method available for use in conjunction with pharmaceutical compositions. The compositions of the present disclosure may be administered alone or may be administered with additional active agents if desired.

The compositions described can be used in the form of a medicinal preparation, for example, in aerosol, solid, semi-solid or liquid form which contains the compounds disclosed as active ingredients. In addition, the compositions may be used in an admixture with an appropriate pharmaceutically acceptable carrier. Such pharmaceutically acceptable carriers include, but are not limited to, organic or inorganic carriers, excipients or diluents suitable for pharmaceutical applications. The active ingredients may be compounded, for example, with the usual non-toxic pharmaceutically acceptable carriers, excipients or diluents for tablets, pellets, capsules, inhalants, suppositories, solutions, emulsions, suspensions, aerosols and any other form suitable for use. Pharmaceutically acceptable carriers for use in pharmaceutical compositions are well known in the pharmaceutical field, and are described, for example, in Remington: The Science and Practice of Pharmacy Pharmaceutical Sciences, Lippincott Williams and Wilkins (A. R. Gennaro editor, $20^{th}$ edition). Such materials are nontoxic to the recipients at the dosages and concentrations employed and include, but are not limited to, water, talc, gum acacia, gelatin, magnesium trisilicate, keratin, colloidal silica, urea, buffers such as phosphate, citrate, acetate and other organic acid salts, antioxidants such as ascorbic acid, peptides, low molecular weight (less than about ten residues) peptides such as, but not limited to, polyarginine, proteins, such as, but not limited to, serum albumin, gelatin, or immunoglobulins, hydrophilic polymers such as, but not limited to, polyvinylpyrrolidinone, amino acids such as, but not limited to, glycine, glutamic acid, aspartic acid, or arginine, monosaccharides, disaccharides, and other carbohydrates including cellulose or its derivatives, lactose, mannitol, glucose, mannose, dextrins, potato or corn starch or starch paste, chelating agents such as, but not limited to, EDTA, sugar alcohols such as mannitol or sorbitol, counterions such as, but not limited to, sodium and/or nonionic surfactants such as, but not limited to, the Tweens, Pluronics or polyethyleneglycol. In addition, the compositions may comprise auxiliary agents, such as, but not limited to, taste-enhancing agents, stabilizing agents, thickening agents, coloring agents and perfumes.

The compositions may be prepared for storage or administration by mixing the active ingredients, each having a desired degree of purity, with physiologically acceptable carriers, excipients, stabilizers, auxiliary agents etc. as is known in the pharmaceutical field. Such compositions may be provided in sustained release or timed release formulations.

The compositions containing the active ingredients may be administered orally in solid dosage forms, such as capsules, tablets, and powders, or in liquid dosage forms, such as elixirs, syrups and suspensions. Furthermore the compositions containing the active ingredients may be administered parenterally, in sterile liquid dosage forms, by transmucosal delivery via solid, liquid or aerosol forms or transdermally via a patch mechanism or ointment. Various types of transmucosal administration include respiratory tract mucosal administration, nasal mucosal administration, oral transmucosal (such as sublingual and buccal) administration and rectal transmucosal administration.

For preparing solid compositions such as, but not limited to, tablets or capsules, the compounds described may be mixed with an appropriate pharmaceutically acceptable carriers, such as conventional tableting ingredients (lactose, sucrose, mannitol, corn starch, potato starch, alginic acid, microcrystalline cellulose, acacia, gelatin, gums, colloidal silicon dioxide, croscarmellose sodium, talc, sorbitol, stearic acid magnesium stearate, calcium stearate, zinc stearate, stearic acid, dicalcium phosphate other excipients, colorants, diluents, buffering agents, disintegrating agents, moistening agents, preservatives, flavoring agents, and pharmacologically compatible carriers) and diluents (including, but not limited to, water, saline or buffering solutions) to form a substantially homogenous composition. The substantially homogenous composition means the components (a compound as described herein and a pharmaceutically acceptable carrier) are dispersed evenly throughout the composition so that the composition may be readily subdivided into equally effective unit dosage forms such as tablets, pills and capsules. The solid compositions described may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact through the stomach or to be delayed in release. A variety of materials can be used for such enteric layers or coatings such materials including a number of polymeric acids and mixtures of polymeric acids with such materials as shellac, cetyl alcohol and cellulose acetate. The active ingredients may also be formulated in rectal compositions such as suppositories or retention enemas, e.g., containing conventional suppository bases such as cocoa butter or other glycerides. The solid compositions may also comprise a capsule, such as hard- or soft-shelled gelatin type containing, for example, surfactants, lubricants, and inert fillers, such as lactose, sucrose, calcium phosphate, and corn starch.

For intranasal administration, intrapulmonary administration or administration by other modes of inhalation, the compositions may be delivered in the form of a solution or suspension from a pump spray container or as an aerosol spray presentation from a pressurized container or nebulizer, with the use of a suitable propellant (e.g., dichlorodifluoromethane, trichlorofluoromethane, dichlorotetrafluoroethane, nitrogen, propane, carbon dioxide or other suitable gas) or as a dry powder. In the case of an aerosol or dry powder format, the amount (dose) of the composition delivered may be determined by providing a valve to deliver a metered amount.

Liquid forms may be administered orally, parenterally or via transmucosal administration. Suitable forms for liquid administration include aqueous solutions, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. For buccal or sublingual administration, the composition may take the form of tablets or lozenges formulated in conventional manners. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compositions may be formulated for parenteral administration. Parenteral administration includes, but is not limited to, intravenous administration, subcutaneous administration, intramuscular administration, intradermal administration, intrathecal administration, intraarticular administration, intracardiac administration, retrobulbar administration and administration via implants, such as sustained release implants The compositions may be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art.

The compositions are administered in a therapeutically effective amount. The therapeutically effective amount will, of course, vary depending upon known factors, such as the pharmacodynamic characteristics of the particular compound or composition and its mode and route of administration; the age, health and weight of the subject; the severity and stage of the disease state or condition; the kind of concurrent treatment; the frequency of treatment; and the effect desired. The total amount of the composition administered will also be determined by the route, timing and frequency of administration as well as the existence, nature, and extent of any adverse side effects that might accompany the administration of the composition and the desired physiological effect. It will be appreciated by one skilled in the art that various conditions or disease states, in particular chronic conditions or disease states, may require prolonged treatment involving multiple administrations.

The following examples are provided to illustrate the applciaiton of several embodiments of the compositions of the present disclosure.

EXAMPLES

Example 1

Preclinical Tests of the Product on Migraine Patients

One embodiment of the composition disclosed was tested on migraine patients in a preclinical trial in hospital-based neurology clinics. Patients having at least one episode of migraine per week for at least one year, with and without aura, were selected from the clinics' database. Twenty-two patients volunteered to participate in the study. Patients were not required to stop current medications to be eligible for the study. The prescribed medicine most often taken by these patients were triptans.

Prior to treatment with the composition of the present disclosure, patients were asked to rate the severity of migraines they experienced from 1 (minor) to 10 (severe, unable to function), the frequency of migraines, and duration (in hours) while taking their previously prescribed medications. The data were recorded and presented in Table 3.

All patients were given a one month supply of the disclosed composition in tablet form. The composition administered is given in Table 2. The patients were instructed to take 2 tablets twice per day with meals for one week and thereafter only two tablets once per day with meals for the remainder of the treatment period (4 weeks). The patients were asked to keep records rating their symptoms while taking the composition of the present disclosure as they did for their previously prescribed medications, as above. After completion of the 5 week administration patients were asked to rate their symptoms as above. The results are shown in Table 3. Patients who had severity 1 migraine were asked to distinguish these headaches from tension or other headaches.

Comparative analysis for headache severity and duration while patients were taking the disclosed composition are tabulated separately in Table 3 and illustrated graphically in FIG. 1. Table 3 and FIG. 1 clearly show that the administration of the composition of the present disclosure significantly reduced the number of migraine headaches (from 5.6 to 2.5). In addition, when a subject experienced a migraine headache while taking the composition of the present disclosure, the severity of migraine headache was reduced (from a scale of 5.1 to 2.1) and the duration of the migraine headache was reduced (from 8.7 hours to 3.3 hours). As shown in FIG. 1, after taking the product for one week, migraine severity begins to decrease, with a significant reduction of migraine severity reported for the fourth and fifth weeks.

Secondary outcome is defined as the patients' feelings of wellness, energy level, mental state, and decrease and/or alleviation of any associated discomforts, particularly any musculoskeletal pains, such as lower back and/or shoulder pain and any tension-type headache. Several subjects also indicated experiencing some kind of anxiety and/or tension-type headache while taking prescribed medications. These subjects expressed that they did not have any anxiety and/or tension type headaches while taking the composition of the present disclosure and that most of their other pains, usually in the lower back and neck, were also relieved. Concomitantly, many patients expressed that they felt very well, and had more energy than previously. Not a single patient reported any adverse side effects due to the treatment protocol.

Furthermore, when subjects stopped taking the composition of the present disclosure, the severity of migraine headaches increased (FIG. 1). In addition, many patients expressed relief from depression they suffered earlier. It is known that frequent migraine headache is usually accompanied by serious depression (Feurmond, J Sharpe I. Ethn Dis. 2005;15(3 Suppl 4):S4-47-8).

Figure 2:
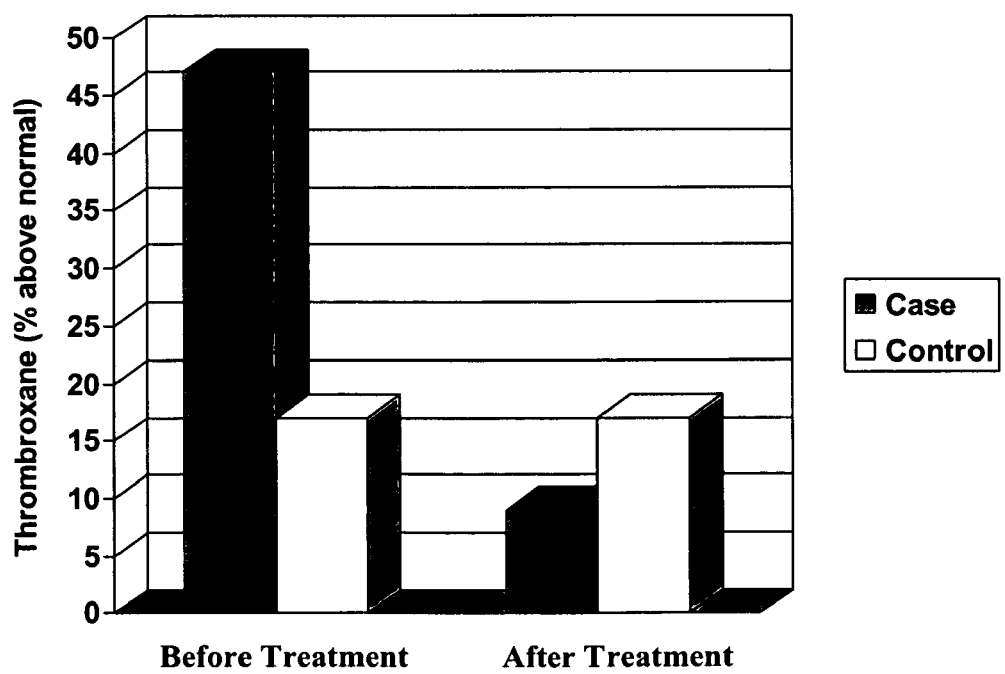
FIG. 2 illustrates the anti-inflammatory effects of one embodiment of the composition of the present disclosure in human subjects as measured by a decrease in thromboxane $B_2$ production.

Furthermore, the levels of the pro-inflammatory mediator thromboxane $B_2$ was measured in both the subjects taking the composition of the present disclosure as described above and in control subjects not taking the composition of the present disclosure. Thromboxane $B_2$ levels were measured both before and after treatment with the composition of the present disclosure. The levels of thromboxane $B_2$ may be used as a measure of neurogenic inflammation in the subjects. As shown in FIG. 2, thromboxane $B_2$ levels were significantly higher in migraine subjects (dark bars, designated case) than in control subjects (light bars, designated control) prior to treatment with the composition illustrated in Table 2. After 5 weeks of treatment as described above, thromboxane $B_2$ levels were significantly decreased in the migraine subjects as compared to their pre-treatment levels. In facts, thromboxane $B_2$ levels were reduced to below the levels of the control subjects. This data clearly shows that the composition described significantly reduces the levels of thromboxane $B_2$ in human subjects. This reduction in thromboxane $B_2$ levels was correlated with a reduction in migraine severity, duration and frequency (see FIG. 1 and Table 3).

Example 2

Preclinical Tests of the Product on Arthritic and Fibromyalgia Patients

One embodiment of the composition disclosed was tested on subjects suffering from arthritis and fibromyalgia. Subjects who reported to the clinics of three privately practicing physicians were recruited. A total of 30 (22 female and 8 male) such patients agreed to participate in this study for 3 weeks without taking any other medications. Within a week 4 (one male and 3 female) patients withdrew from this study since they had to revert back to some pain management treatment. A total of 26 patients agreed to participate in the study and completed the study.

It is difficult to distinguish aches and pains due to arthritis from those due to fibromyalgia. Callahan and Pincus (Arthritis and Rheumatism 1990;33:1317-1322) developed a questionnaire that includes two scales: 1) difficulty in activity of daily living (D-ADL), and 2) pain visual analog scale (P-VAS) in order to delineate between arthritis and fibromyalgia. A series of questions were asked to individuals to estimate the scores for D-ADL and P-VAS. The questions are illustrated in Table 4 to estimate D-ADL.

The P-VAS rates, on a scale of 0-10, the severity of pain associated with each activity with 0 being none and 10 being the maximum. To evaluate the Callahan and Pincus questionnaire, the average of the score from the D-ADL is used to divide the score on the P-VAS. If the number of P-VAS/D-ADL is less than 3, the patient is diagnosed with arthritis, if the patients score is more than 5 the patient is diagnosed with fibromyalgia. Seven patients were thus categorized as arthritic and were further examined for their joint pain and joint swelling by using the Lequesne Index (Lequesne M et al. Scand. J. Rheumatol. 1982;22:2290-2296).

The remaining 19 were categorized as fibromyalgic patients, and were further asked to score on their physical and mental health conditions as follows: (i) any physical impairment (0-10); (ii) days per week the subject felt "good" (1-7); (iii) daily fatigue (0-10); (iv) feeling tired upon awakening (0-10); (v) stiffness (0-10); (vi) anxiety (0-10); (vii) depression (0-10); and (viii) numbness (0-10). Fibromyalgia patients were also examined for tender points on their body.

After having all the above score and examinations completed, each patient was given the composition of the present disclosure in tablet form and instructed to take 2 tablets with a meal in the morning and the evening for 3 weeks. All the subjects reported compliance with the treatment protocol and no adverse effects associated with the treatment protocol. After completing this treatment protocol the above referenced health conditions were evaluated. The results are presented in the following tables separately for arthritic (Table 5) and fibromyalgic subjects (Table 6).

Tables 5 and 6 show that the subjects benefited by taking the composition of the present disclosure for only three weeks. Fibromyalgic patients showed a greater improvement in a number of areas as compared to the arthritic patients. For fibromyalgic subjects, significant improvement was observed in: P-VAS (9.01±1.0 to 1.5±0.8); ability to dress themselves (1.6±0.6 to 1.0±0.9), bending down (2.10±0.9 to 1.0±0.2), physical impairment (3.03±1.0 to 1.8±0.5); number of says per week feeling "good" (2.5±1.3 to 5.5±1.2); tiredness upon awakening (6.9±4.4 to 1.9±0.8); and stiffness (4.3±2.1 to 1.7±0.4). Improvements were observed in other areas as well.

For arthritic subjects, improvements were noted in: P-VAS (7.4±1.4 to 5.7±1.1); ability to dress themselves (3.3±1.3 to 2.7±1.1); and getting in a car (3.5±1.3 to 2.7±1.02). Improvements were observed in other areas as well. The decreased impact on arthritic subjects as compared to fibromyalgic subjects may be due to the decreased severity of pain and joint swelling observed in arthritic subjects as compared to fibromyalgic subjects. As a result, the arthritic subjects may have noted less dramatic improvement over the course of treatment. Furthermore, the short course of treatment may not have been sufficient for dramatic improvement in the arthritic subjects. For example, the Lequesne Index showed a lowering trend in swelling of joints which may be due to the short treatment course. It is likely that longer treatment duration would result a more significant beneficial changes in the joint swelling as well as the other criteria analyzed.

The foregoing description illustrates and describes the methods and compounds of the present disclosure. Nothing herein is to be construed as an admission that the inventors are not entitled to antedate such disclosure by virtue of prior disclosure. Additionally, the disclosure shows and describes only certain embodiments of the methods and compounds but, as mentioned above, it is to be understood that the teachings of the present disclosure are capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. All references cited herein are incorporated by reference as if fully set forth in this disclosure.

TABLE 1

| COMPONENT | RANGE |
|---|---|
| Beta carotene | (100-1000) IU |
| Thiamine HCl | (5-200) mg |
| $B_2$ (Riboflavin) | (5-250) mg |
| $B_6$ (pyridoxine HCl or pyridoxal 5-phosphate) | (5-500) mg |
| Vitamin $B_{12}$ (Me or OH) | (100-2000) µg |
| Folate | (100-2000) µg |
| Biotin | (5-500) µg |
| Vitamin E (succinate) | (5-1500) IU |
| Vitamin C (ascorbic acid) | (5-2000) mg |
| Mg (citrate) | (10-1000) mg |
| Zn (amino acid chelate) | (1-100) mg |
| Se (amino acid chelate) | (5-500) µg |
| Mn (amino acid chelate) | (1-500) mg |
| Glucosamine Sulfate | (50-2000) mg |
| Methylsulfonylmethane | (20-2000) mg |
| Glutathione (reduced) | (2-250) mg |
| Niacinamide | (5-500) mg |
| CoQ10 | (1-500) mg |
| N-Acetyl-tyrosine | (5-1000) mg |
| α-lipoic acid | (1-1000) mg |
| Hydroxcitric acid | (5-500) mg |
| S-Adenosylmethionine | (5-500) mg |
| Pantothenic acid (Mg) | (5-500) mg |
| Chondroitin Sulfate | (5-1500) mg |

TABLE 2

| COMPONENT | AMOUNT |
|---|---|
| Beta carotene | 300 IU |
| Thiamine HCl | 25 mg |
| $B_2$ (Riboflavin) | 15 mg |
| B6 (pyridoxine HCl and pyridoxal 5-phosphate) | 25 mg |
| Vitamin B12 (Me & OH) | 600 µg |
| Folate | 550 µg |
| Biotin | 100 µg |
| Vitamin E (succinate) | 30 IU |
| Vitamin C (ascorbic acid) | 50 mg |
| Mg (citrate) | 100 mg |
| Zn (amino acid chelate) | 5 mg |
| Se (amino acid chelate) | 30 µg |
| Mn (amino acid chelate) | 2 mg |
| Glucosamine Sulfate | 250 mg |
| Methylsulfonylmethane | 150 mg |
| Glutathione (reduced) | 7 mg |
| Niacinamide | 50 mg |
| CoQ10 | 5 mg |
| N-Acetyl-tyrosine | 100 mg |
| A-lipoic acid | 50 mg |
| Hydrocitric acid | 25 mg |
| S-Adenosylmethionine | 50 mg |
| Pantothenic acid (Mg) | 50 mg |
| Chondroitin Sulfate | 100 mg |

TABLE 3

Comparative Demographics and Headache Characteristics

| Parameters | Pre-Administration N = 22 | Administration Period n = 22 | P-values |
|---|---|---|---|
| Age in years | 46.8 ± 8.6 | 46.8 ± 8.6 | Ns |
| Sex | 19 F | 19 F | Ns |
| No. of Migraines | 5.6 ± 2.1 | 2.5 ± 1.4 | <0.001 |
| Duration in hrs | 8.7 ± 5.5 | 3.3 ± 1.9 | <0.001 |
| Severity (1 to 10) | 5.1 ± 3.5 | 2.1 ± 1.1 | <0.001 |
| Tension-type Headache | Yes | None | — |
| Secondary outcomes | None | Yes | — |

TABLE 4

Questions used to assess the D-ADL score

| D-ADL | w/o ANY difficulty (1) | with SOME difficulty (2) | with MUCH difficulty (3) | UNABLE (4) |
|---|---|---|---|---|
| 1. Dress yourself, including tying shoelaces and doing buttons? | | | | |
| 2. Get in and out of bed? | | | | |
| 3. Lift a full cup or glass to your mouth? | | | | |
| 4. Walk outdoors on flat ground? | | | | |
| 5. Wash and dry your entire body? | | | | |
| 6. Bend down? | | | | |
| 7. Turn water faucet? | | | | |
| 8. Get in and out of a car? | | | | |

TABLE 5

Clinical Efficacy on Arthritic Patients.
Number of patients (n) = 7 (male = 4, female = 3),
Mean age = 47.8 years
Mean of disease duration = 8.6 years

| Conditions monitored | Pre-treatment | Post-treatment | Clinical evaluations |
|---|---|---|---|
| Dress yourself, including tying shoelaces and button | 2.7 ± 1.0 | 2.03 ± 1.02 | Good |
| Get in and out of bed | 2.04 ± 0.9 | 1.2 ± 0.63 | Better |
| Lift a full cup or glass to your mouth | 2.3 ± 1.03 | 1.9 ± 0.72 | Good |
| Walk outdoors on flat ground | 3.01 ± 1.2 | 2.2 ± 0.91 | Better |
| Wash and dry your entire body | 2.8 ± 1.0 | 2.02 ± 0.8 | Better |
| Bend down | 3.3 ± 1.3 | 2.7 ± 1.01 | Much better |
| Get in and out of a car | 3.5 ± 1.3 | 2.7 ± 1.02 | Much better |
| Pain on visual scale | 7.4 ± 1.4 | 5.7 ± 1.1 | Better |
| Swelling of joints (Lequesne Index) | 7.5 ± 2.5 | 6.3 ± 2.2 | Lower trend |

TABLE 6

Clinical Efficacy on Fibromyalgia.
Number of patients (n) = 19 (male = 3, female = 16),
Mean age = 45.6 years
Mean disease duration = 6.6 years

| Conditions Monitored | Pre-treatment | Post-treatment | Clinical evaluations |
|---|---|---|---|
| Dress yourself, including tying shoelaces and button | 1.6 ± 0.6 | 1.0 ± 0.4 | Much better |
| Get in and out of bed | 1.5 ± 0.5 | 1.02 ± 0.2 | Better |
| Lift a full cup or glass to your mouth | 1.3 ± 0.5 | 0.8 ± 0.3 | Better |
| Walk outdoors on flat ground | 1.7 ± 0.4 | 1.0 ± 0.3 | Better |
| Wash and dry your entire body | 1.0 ± 0.4 | 0.0 ± 0.0 | Better |
| Bend down | 2.01 ± 0.9 | 1.0 ± 0.2 | Much better |
| Get in and out of a car | 0.7 ± 0.02 | 0.0 ± 0.0 | Good |
| Pain on visual scale | 9.0 ± 1.0 | 1.5 ± 0.8 | Extremely well |
| Physical impairment | 3.03 ± 1.0 | 1.8 ± 0.5 | Much better |
| days per week the subject felt "good" | 2.5 ± 1.3 | 5.5 ± 1.2 | Much better |
| Fatigue | 7.8 ± 3.5 | 2.1 ± 0.6 | Relieved |
| Feeling tired upon awakening | 6.9 ± 4.4 | 1.9 ± 0.8 | Much better |
| Stiffness | 4.3 ± 2.1 | 1.7 ± 0.4 | Much better |
| Anxiety | 3.2 ± 2.8 | 1.6 ± 1.1 | Better |
| Depression | 4.8 ± 2.4 | 2.2 ± 1.3 | Better |
| Tender points (0-18) | 11.7 ± 4.2 | 5.3 ± 1.9 | Improved |

What is claimed is:

1. A composition for the treatment of inflammation in a subject, the composition comprising:
 a) between about 100 and 1000 IU beta carotene;
 b) between about 5 and 200 mg thiamine;
 c) between about 5 and 250 mg vitamin $B_2$;
 d) between about 5 and 500 mg vitamin $B_6$;
 e) between about 100 and 2000 μg vitamin $B_{12}$;
 f) between about 100 and 2000 μg folate;
 g) between about 5 and 500 μg biotin;
 h) between about 5 and 1500 IU vitamin E;
 i) between about 5 and 2000 mg vitamin C;
 j) between about 10 and 1000 mg magnesium;
 k) between about 1 and 100 mg zinc;
 l) between about 5 and 500 μg selenium;
 m) between about 1 and 500 mg manganese;
 n) between about 50 and 2000 mg glucosamine sulfate;
 o) between about 20 and 2000 mg methylsulfonylmethane;
 p) between about 2 and 250 mg glutathione;
 q) between about 5 and 500 mg niacinamide;
 r) between about 1 and 500 mg coenzyme Q10;
 s) between about 5 and 1000 mg N-acetyl tyrosine;
 t) between about 1 and 1000 mg α-lipoic acid;
 u) between about 5 and 500 mg hydroxycitric acid;
 v) between about 5 and 500 mg S-adenosylmethionine;
 w) between about 5 and 500 mg pantothenic acid; and
 x) between about 5 and 1500 mg chondroitin sulfate.

2. The composition of claim 1, wherein:
 said vitamin $B_{12}$ is selected from the group consisting of methylcobalamin, hydroxycobalamin and a combination thereof;
 said vitamin $B_6$ is selected from the group consisting of pyridoxal-5-phosphate, pyridoxine HCl and a combination thereof; and
 said magnesium is a citrate salt.

3. The composition of claim 1, wherein at least one of ingredients (a) to (x) is in a chelated form.

4. The composition of claim 1, wherein:
 said vitamin $B_{12}$ is selected from the group consisting of methylcobalamin, hydroxycobalam in and a combination thereof;
 said vitamin $B_6$ is selected from the group consisting of pyridoxal-5-phosphate, pyridoxine HCl and a combination thereof;
 said magnesium is a citrate salt;
 said thiamine is a HCl salt;
 said vitamin E is a succinate ester;
 said glutathione is present in a reduced form;
 said pantothenic acid is present as a magnesium salt; and
 at least one of said zinc, manganese or selenium is present as an amino acid chelate.

5. A method of treating or reducing inflammation in a subject in need thereof, said method comprising the step of administering to said subject a therapeutically effective amount of a pharmaceutical composition comprising:
 a) between about 100 and 1000 IU beta carotene;
 b) between about 5 and 200 mg thiamine;
 c) between about 5 and 250 mg vitamin $B_2$;
 d) between about 5 and 500 mg vitamin $B_6$;
 e) between about 100 and 2000 μg vitamin $B_{12}$;
 f) between about 100 and 2000 μg folate;
 g) between about 5 and 500 μg biotin;
 h) between about 5 and 1500 IU vitamin E;
 i) between about 5 and 2000 mg vitamin C;
 j) between about 10 and 1000 mg magnesium;
 k) between about 1 and 100 mg zinc;
 l) between about 5 and 500 μg selenium;
 m) between about 1 and 500 mg manganese;
 n) between about 50 and 2000 mg glucosamine sulfate;
 o) between about 20 and 2000 mg methylsulfonylmethane;
 p) between about 2 and 250 mg glutathione;
 q) between about 5 and 500 mg niacinamide;
 r) between about 1 and 500 mg coenzyme Q10;
 s) between about 5 and 1000 mg N-acetyl tyrosine;
 t) between about 1 and 1000 mg α-lipoic acid;
 u) between about 5 and 500 mg hydroxycitric acid;
 v) between about 5 and 500 mg S-adenosylmethionine;
 w) between about 5 and 500 mg pantothenic acid; and
 x) between about 5 and 1500 mg chondroitin sulfate.

6. The method of claim 5, wherein:
said vitamin $B_{12}$ is selected from the group consisting of methylcobalamin, hydroxycobalamin and a combination thereof;
said vitamin $B_6$ is selected from the group consisting of pyridoxal-5-phosphate, pyridoxine HCl and a combination thereof; and
said magnesium is a citrate salt.

7. The method of claim 5, wherein at least one of ingredients (a) to (x) is in a chelated form.

8. The method of claim 5, wherein:
said vitamin $B_{12}$ is selected from the group consisting of methylcobalamin, hydroxycobalamin and a combination thereof;
said vitamin $B_6$ is selected from the group consisting of pyridoxal-5-phosphate, pyridoxine HCl and a combination thereof;
said magnesium is a citrate salt;
said thiamine is a HCl salt;
said vitamin E is a succinate ester;
said glutathione is present in a reduced form;
said pantothenic acid is present as a magnesium salt; and
at least one of said zinc, manganese or selenium is present as an amino acid chelate.

9. A method of reducing the levels of a pro-inflammatory mediator associated with inflammation in a subject in need thereof, said method comprising the step of administering to said subject a therapeutically effective amount of a pharmaceutical composition comprising:
a) between about 100 and 1000 IU beta carotene;
b) between about 5 and 200 mg thiamine;
c) between about 5 and 250 mg vitamin $B_2$;
d) between about 5 and 500 mg vitamin $B_6$;
e) between about 100 and 2000 µg vitamin $B_{12}$;
f) between about 100 and 2000 µg folate;
g) between about 5 and 500 µg biotin;
h) between about 5 and 1500 IU vitamin E;
i) between about 5 and 2000 mg vitamin C;
j) between about 10 and 1000 mg magnesium;
k) between about 1 and 100 mg zinc;
l) between about 5 and 500 µg selenium;
m) between about 1 and 500 mg manganese;
n) between about 50 and 2000 mg glucosamine sulfate;
o) between about 20 and 2000 mg methylsulfonylmethane;
p) between about 2 and 250 mg glutathione;
q) between about 5 and 500 mg niacinamide;
r) between about 1 and 500 mg coenzyme Q10;
s) between about 5 and 1000 mg N-acetyl tyrosine;
t) between about 1 and 1000 mg α-lipoic acid;
u) between about 5 and 500 mg hydroxycitric acid;
v) between about 5 and 500 mg S-adenosylmethionine;
w) between about 5 and 500 mg pantothenic acid; and
x) between about 5 and 1500 mg chondroitin sulfate.

10. The method of claim 9, wherein:
said vitamin $B_{12}$ is selected from the group consisting of methylcobalamin, hydroxycobalamin and a combination thereof;
said vitamin $B_6$ is selected from the group consisting of pyridoxal-5-phosphate, pyridoxine HCl and a combination thereof; and
said magnesium is a citrate salt.

11. The method of claim 9, wherein at least one of ingredients (a) to (x) is in a chelated form.

12. The method of claim 9, wherein:
said vitamin $B_{12}$ is selected from the group consisting of methylcobalamin, hydroxycobalamin and a combination thereof;
said vitamin $B_6$ is selected from the group consisting of pyridoxal-5-phosphate, pyridoxine HCl and a combination thereof;
said magnesium is a citrate salt;
said thiamine is a HCl salt;
said vitamin E is a succinate ester;
said glutathione is present in a reduced form;
said pantothenic acid is present as a magnesium salt; and
at least one of said zinc, manganese or selenium is present as an amino acid chelate.

13. The method of claim 9 where said pro-inflammatory mediator is thromboxane $B_2$.

14. The method of claim 9 where said thromboxane $B_2$ is associated with migraine headache, arthritis or fibromyalgia.

* * * * *